US006936811B2

(12) United States Patent  
Kibar (10) Patent No.: US 6,936,811 B2  
(45) Date of Patent: Aug. 30, 2005

(54) METHOD FOR SEPARATING MICRO-PARTICLES

(75) Inventor: Osman Kibar, New York, NY (US)

(73) Assignee: Genoptix, Inc., San Diego, CA (US)

( * ) Notice: Subject to any disclaimer, the term of this patent is extended or adjusted under 35 U.S.C. 154(b) by 518 days.

(21) Appl. No.: 09/843,902

(22) Filed: Apr. 27, 2001

(65) Prior Publication Data

US 2005/0094232 A1 May 5, 2005

Related U.S. Application Data

(60) Provisional application No. 60/248,451, filed on Nov. 13, 2000.

(51) Int. Cl.⁷ ............................ H05H 3/02; C12N 13/00
(52) U.S. Cl. .................................... 250/251; 435/173.1
(58) Field of Search ........................ 250/251; 435/173.1

(56) References Cited

U.S. PATENT DOCUMENTS

| | | | |
|---|---|---|---|
| 3,826,899 A | 7/1974 | Ehrlich et al. |
| 4,253,846 A | 3/1981 | Smythe et al. |
| 4,386,274 A | 5/1983 | Altshuler |
| 4,460,667 A | 7/1984 | Landa |
| 4,756,427 A | 7/1988 | Göhde |
| 4,886,360 A | 12/1989 | Finlan |
| 4,939,081 A | 7/1990 | Figdor et al. |
| 5,374,556 A | 12/1994 | Bennett et al. |
| 5,472,550 A | 12/1995 | Periasamy |
| 5,667,286 A | 9/1997 | Shull et al. |
| 5,752,606 A | 5/1998 | Wilson et al. |
| 5,773,298 A | 6/1998 | Lynggaard et al. |
| 5,834,208 A | 11/1998 | Sakano |
| 5,942,443 A | 8/1999 | Parce et al. |
| 5,950,071 A | 9/1999 | Hammond et al. |
| 5,998,152 A | 12/1999 | Lynch et al. |
| 6,008,010 A | 12/1999 | Greenberger et al. |
| 6,149,789 A | 11/2000 | Benecke et al. |
| 6,221,654 B1 | 4/2001 | Quake et al. |
| 6,224,732 B1 | 5/2001 | Imasaka et al. |
| 6,242,209 B1 | 6/2001 | Ransom et al. |
| 6,280,960 B1 | 8/2001 | Carr |
| 6,280,967 B1 | 8/2001 | Ransom et al. |
| 6,287,758 B1 | 9/2001 | Okun et al. |
| 6,344,325 B1 | 2/2002 | Quake et al. |
| 6,355,491 B1 | 3/2002 | Zhou et al. |
| 6,387,331 B1 | 5/2002 | Hunter |
| 6,395,480 B1 | 5/2002 | Hefti |
| 6,399,397 B1 | 6/2002 | Zarling et al. |
| 6,408,878 B2 | 6/2002 | Unger et al. |
| 6,411,838 B1 | 6/2002 | Nordstrom et al. |
| 6,485,905 B2 | 11/2002 | Hefti |
| 6,507,400 B1 | 1/2003 | Pina et al. |
| 6,514,722 B2 | 2/2003 | Palsson et al. |
| 6,518,056 B2 | 2/2003 | Schembri et al. |
| 6,534,308 B1 | 3/2003 | Palsson et al. |
| 6,540,895 B1 | 4/2003 | Spence et al. |
| 6,566,079 B2 | 5/2003 | Hefti |
| 6,624,940 B1 | 9/2003 | Grier et al. |
| 6,740,497 B2 | 5/2004 | Allbritton et al. |
| 6,744,038 B2 | 6/2004 | Wang et al. |
| 6,778,724 B2 | 8/2004 | Wang et al. |
| 6,797,942 B2 | 9/2004 | Grier et al. |
| 2002/0025529 A1 | 2/2002 | Quake et al. |
| 2002/0037542 A1 | 3/2002 | Allbritton et al. |
| 2002/0058332 A1 | 5/2002 | Quake et al. |
| 2002/0181837 A1 | 12/2002 | Wang et al. |
| 2003/0008364 A1 | 1/2003 | Wang et al. |
| 2003/0032204 A1 | 2/2003 | Walt el al. |
| 2003/0047676 A1 | 3/2003 | Grier et al. |

FOREIGN PATENT DOCUMENTS

| | | |
|---|---|---|
| EP | 0556748 A3 | 8/1993 |
| EP | 0556748 A2 | 8/1993 |
| EP | 0635994 A1 | 1/1995 |
| EP | 0635994 B1 | 9/1998 |
| EP | 0556748 B1 | 10/1998 |
| JP | 9-43434 A | 2/1997 |
| WO | WO 01/40454 A1 | 6/2001 |
| WO | WO 01/68110 A1 | 9/2001 |
| WO | WO 02/22774 A1 | 3/2002 |
| WO | WO 02/39104 A1 | 5/2002 |

OTHER PUBLICATIONS

MacDonald et al., "Trapping and Manipulation of Low–Index Particles in a Two–Dimensional Interferometric Optical Trap" (2001) Optics Letters, 26(12) 863–865.*

Molloy et al., "Optical Tweezers in a New Light" (2003) J. Modern Optics, 50(10), 1501–1507.*

Zemánek et al., "Optical Trapping of Rayleigh Particles Using a Gaussian Standing Wave" (1998) Optics Comm., 151(4,5,6), 273–285.*

Molloy et al., "Lights, Action: Optical Tweezers" (2002) Contemp. Physics, 43(4), 241–258.*

Arlt et al, "Moving Interference Patterns Created Using The Angular Doppler Effect", Optics Express, 10, 16, 2002, 844–852.

Ashkin, "The Pressure Of Laser Light", Scientific American, 226, 2, 1972, 63–71.

Buican, "Automated Cell–Separation Techniques Based On Optical Trapping", ACS Symposium Series, 464, 1991, 59–72.

*Experimental Biochemistry*, 2$^{nd}$ Edition, J.M. Clark & R.L. Switzer, eds., Section II, W.H. Freeman and Co., New Yor, 1997, 73–74.

(Continued)

Primary Examiner—Jean C. Witz  
Assistant Examiner—Susan Hanley  
(74) Attorney, Agent, or Firm—O'Melveny & Myers LLP (57) ABSTRACT

A system and method for separating particles is disclosed in which the particles are exposed to a moving light intensity pattern which causes the particles to move a different velocities based on the physical properties of the particles. This system and method allows particles of similar size and shape to be separated based on differences in the particles dielectric properties.

58 Claims, 4 Drawing Sheets

OTHER PUBLICATIONS

Imasaka, et al., "Optical Chromatography. A New Tool For Separation Of Particles", Analusis Magazine, 26, 5, 1998 M 53–M55.

Markx, et al., "Dielectrophoretic Separation of Bacteria Using A Conductivity Gradient", Journal of Biotechnology, 51, 1996.

Markx, et al., "The Dielectrophoretic Levitation of Latex Beads, with Reference To Field–Flow Fractionation", Journal Of Physics D: Applied Physics, 20, 17, 1997, 2470–2477.

Pethig, et al., "Applications Of Dielectrophoresis in Biotechnology", TIBTECH, 15, 10, Oct. 1997, 426–432.

Prieve, "Use Of Optical Forces To Detach Single Microscopic Particles Adhering To Flat Surfaces in Aqueous Media", Proceedings Of The Annual Meeting Of The Adhesion Society, 20$^{th}$, 1997, 151–153.

Yang, et al., "Dielectric Properties of Human Leukocyte Subpopulations Determined By Electrorotation As A Cell Separation Criterion", Biophysical Journal, 76, Jun. 1999, 3307–3314.

Ashkin et al, "Force Generation Of Organelle Transport Measured In Vivo By An Infrared Laser Trap", Nature, 348, Nov. 22, 1990, 346–348.

Caldwell, "Field–Flow Fractionation", Analytical Chemistry, 60, 17, Sep. 1, 1988, 959–971.

Davies et al, "Optically Controlled Collisions Of Biological Objects", SPIE, 3260, Jan. 25–28. 1998, 15–22.

Dholakia et al, "Optical Tweezers: The Next Generation", Physics World, Oct. 2002, 31–35.

Esener, Center For Chips With Heteroageneously Integrated photonics (CHIPS), DARPA Opto Centers Kickoff, Nov. 8, 2000, Dana Point, CA.

Flynn et al, "Parallel Transport Of Biological Cells Using Individually Addressable VCSEL Arrays As Optical tweezers", Sensors & Actuators B, 87, 2002, 239–243.

Imasaka et al, "Optical Chromatography", Analytical Chemistry, 67, 11, Jun. 1, 1995, 1763–1765.

Sasaki et al, "Optical Trapping Of A Metal Particle & A Water Droplet By A Scanning Laser Beam", Appl. Phys. Lett., 60, 7, Feb. 17, 1992, 807–809.

Shikano et al, "Separation Of A Single Cell By Red–Laser Manipulation", Applied Physics Letters, 75, 17, Oct. 25, 1999, 2671–2673.

Sonek et al, "Micromanipulation & Physical Monitoring Of Cells Using Two–Photon Excited Fluorescence In CW Laser Tweezers", SPIE, 2678, Jan. 28–Feb. 1, 1996, 62–68.

Wang et al, "All Optical Switching Of Biological Samples In A Microfluidic Device", International Phonics Conference 2000, Dec. 12–15, 2000, Hsinchu, Taiwan.

Wang et al, "Integration Of Optoelectronic Array Devices For Cell Transport & Sorting", Photonics West 2001, Jan. 20–26, 2001, San Jose, CA.

Wei et al, Laser Trapping Microscopy As A Diagnostic Technique For The Study Of Cellular Response & Laser––Cell Interactions, SPIE, 2983, Feb. 10–11, 1997, 22–28.

Zahn et al, "Fluorimetric Multiparameter Cell Assay At The Single Cell Level Fabricated By Optical Tweezers", FEBS Letters, 443, 1999, 337–340.

Imasaka et al, Optical Chromatography, Analytical Chemistry, vol. 67, No. 11, Jun. 1, 1995, pp. 1763–1765.

Fuhr, et al., "Force Measurements Of Optical Tweezers in Electro–Optical Cages", Appl. Physics A, A67, (4). 1998, pp. 385–390.

Tsai, et al., "Applications Of Optical Tweezers And An Integrated Force Measurement Module For Biomedical Research", Proceedings of the SPIE, 4082, July 2000, pp. 213–221.

* cited by examiner

METHOD FOR SEPARATING MICRO-PARTICLES

RELATED APPLICATIONS

This application is related to and claims priority from provisional Application Ser. No. 60/248,451 filed Nov. 13, 2000, which is incorporated by reference as if fully set forth herein.

FIELD OF THE INVENTION

This invention relates to systems and methods for separating micro-particles and/or nano-particles. More particularly, this invention relates to systems and methods for separating micro-particles and/or nano-particles by using a light source to create a separation force on the particles based on their physical properties.

BACKGROUND OF THE INVENTION

At the present, there are sorting methods to separate particles, such as cells and other biological entities, based on their size, density, and charge, but none that sort based on optical dielectric properties. For example, laser tweezers been described that use the interaction of light with a particle to move the particle around. However, in this case, a priori knowledge of which particle to move is required for the tweezers to be used as a sorting mechanism. In other words, tweezers are more of a 'manipulation and/or transportation' tool, rather than a 'sorting' tool. Thus, current methods and systems for separating particles require prior identification of the particles to be separated.

There is a need for a system and method for separating particles which does not require prior identification of the particles to be separated. There is also a need for a system and method for separating particles which does not damage the particles.

SUMMARY OF THE INVENTION

These needs and others are satisfied by a system and method for separating particles according to the present invention which comprises means for creating a light intensity pattern in the vicinity of the particles and means for moving the light intensity pattern with respect to the particles. The means for creating a light intensity pattern can comprise a light source for producing two light beams aimed to interfere with each other in the vicinity of the two particles.

In one embodiment, the system comprises a beam splitter and a reflector. In this embodiment, the light source is configured to produce a light beam aimed at the beam splitter. The beam splitter is configured to split the light beam into a first light beam directed toward the particles and a second light beam directed toward the reflector. The reflector is configured to redirect the second light beam toward the particles such that the first and second light beams interfere creating a light intensity pattern in the vicinity of the particles.

An actuator can be connected to the reflector for moving the reflector to move the light intensity pattern. Alternatively, the actuator can be connected to the light source and beam splitter for moving the light source and beam splitter.

It is also possible to move the particles relative to the light intensity pattern to create the moving light intensity pattern. In order to do this, the particles can be carried on a slide connected to an actuator configured to move the slide relative to the light intensity pattern.

The light intensity pattern can also be moved by using a phase modulator to modulate the phase of one of the two light beams with respect to the other. This causes the light intensity pattern created by the interference of the light beams to move spatially. The phase modulator can be place in the path of either the first light beam or second light beam. Alternatively, an amplitude modulator can be used, in which case the interference pattern will move temporally.

Any material that responds to optical sources may be utilized with these inventions. In the biological realm, examples would include cells, organelles, proteins and DNA, and in the non-biological realm could include metals, semiconductors, insulators, polymers and other inorganic materials.

Preferably, the light source comprises a laser producing a light beam having a wavelength of between 0.31 $\mu$m and 1.8 $\mu$m. Using a light beam in this wavelength range minimizes the chance that damage will be caused to the particles if they are living cells or biological entities. Even more preferably, the light beam wavelength range could be 0.8 $\mu$m and 1.8 $\mu$m. Good, commercially available lasers are available which produce a light beam having a wavelength of 1.55 $\mu$m.

In an alternative embodiment, the system comprises a light source and an optical mask. The light source is configured for producing a light beam directed through the optical mask toward the particles. The optical mask creates a light intensity pattern in the vicinity of the particles. An actuator can be connected to the light source and optical mask for moving the light source and optical mask to create a moving light intensity pattern. Alternatively, the optical mask can be specially configured for producing a moving light intensity pattern in the vicinity of the at least two particles. Another alternative is to include a phase modulator positioned in the light beam path for modulating the phase of the light beam to create a moving light intensity pattern.

In yet another embodiment the system can comprise a plurality of light sources positioned adjacent to each other for producing a plurality of light beams directed toward the particles. The light beams can be aimed to slightly overlap each other to create a light intensity pattern. An actuator can be included for moving the plurality of light sources, thus causing the light intensity pattern to move spatially. Alternatively, the light beams can be dimmed and brightened in a pattern for creating a temporally moving light intensity pattern.

A method for separating particles according to the present invention comprises the steps of: applying a light source to create a light intensity pattern, exposing particles to the light intensity pattern producing force on each particle and moving the light intensity pattern with respect to the particles causing the particles to move with the light intensity pattern at velocities related to their respective physical properties. If the particles have different physical properties they will move at a different velocity causing the particles to separate.

Preferably, the step of applying a light source comprises interfering at least two optical light beams as discussed herein with respect to one embodiment of a system according to the present invention.

Alternatively, the step of applying a light source can comprise using an optical mask to create the light intensity pattern. The optical mask can comprise an amplitude mask, a phase mask, a holographic mask, or any other suitable mask for creating a light intensity pattern.

In another embodiment of a method according to the present invention the step of applying a light source can comprise periodically dimming and brightening a plurality of light sources to create the light intensity pattern.

Preferably, the light intensity pattern comprises at least two peaks and at least two valleys. The light intensity pattern can be periodic, sinusoidal, nonsinusoidal, constant in time, or varying in time. If the light intensity pattern is periodic, the period can be optimized to create separation between particles.

In one embodiment, the method comprises moving the light intensity pattern at a constant velocity. The velocity of the light intensity pattern can be optimized to cause separation based on the physical properties the particles.

In an alternative embodiment, the method comprises allowing the at least two particles to separate, and then suddenly "jerking" the light intensity pattern to cause particles with different physical properties to fall into different valleys of a potential pattern created by the light intensity pattern.

The method light intensity pattern can be tuned to a resonant frequency corresponding to the physical properties of one type of particles to optimize separation of that type of particle. The light intensity pattern can be applied in multiple dimensions and the period of the light intensity pattern can be varied in each dimension.

The particles can be carried in a medium, such as a fluidic medium, which can be either guided or non-guided. If the medium is guided it can include fluidic channels.

The method can also include superimposing a gradient onto the light intensity pattern. The gradient can be spatially constant or varying and can comprise temperature, pH, viscosity, etc. Additional external forces can also be applied, such as magnetism, electrical forces, gravitational forces, fluidic forces, frictional forces, electromagnetic forces, etc., in a constant or varying fashion.

A monitoring and/or feedback system can also be included for monitoring the separation between particles and providing feedback information as to separation and location of particles.

Further object, features and advantages of the present invention will become apparent from the following description and drawings.

DETAILED DESCRIPTION OF THE PREFERRED EMBODIMENTS

In accordance with the present invention, a system and method for separating particles is described that provides distinct advantages when compared to those of the prior art. The invention can best be understood with reference to the accompanying drawing figures.

Referring now to the drawings, a system according the present invention is generally designated by reference numeral 10. The system 10 is configured to generate a moving light intensity pattern that produces a force on the particles to be separated. The force causes the particles to move at velocities related to certain physical properties of each particle, such as the particle's optical dielectric constant. Particles with different physical properties will move at different velocities causing the particles to separate based on their physical properties.

Figure 1A:
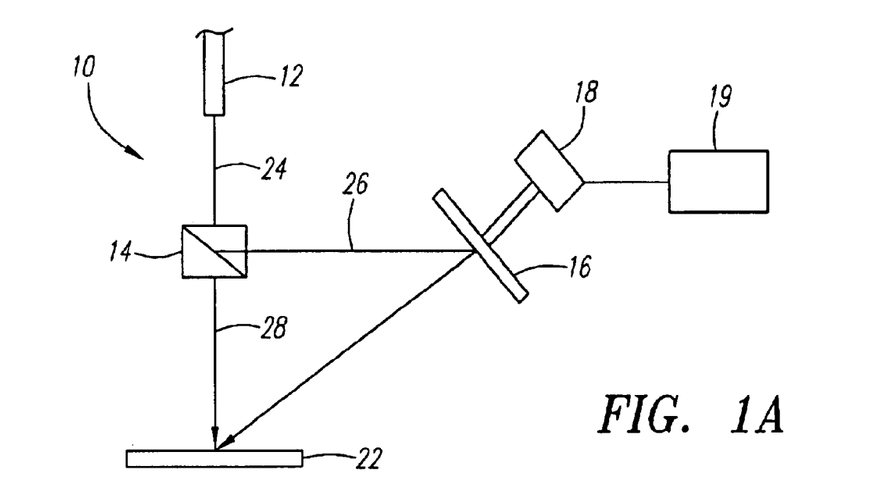
FIGS. 1A, 1B, 2A, 2B and 3 are block diagrams of various embodiments of a system according to the present invention.

One embodiment of a system 10 according to the present invention is shown in FIG. 1. In this embodiment, the system 10 comprises a light source 12, a beam splitter 14, and a reflector 16. A motor 18 can be connected to the reflector 16 for moving or rotating the reflector 16. A control system 19 is connected to the motor 18 for controlling operation of the motor 18 and thus movement of the reflector 16.

The particles to be separated can be placed in a medium on a slide 22. In one embodiment of the invention, the slide 22 includes a non-guided fluidic medium, such as water. In another embodiment, shown in FIG. 6, the slide 22 includes fluidic channels 500, 502 and 504 through which the particles 410, 412 travel.

The medium can be non-guided or guided. One example of a guided medium is a medium comprising fluidic channels as is well known in the art.

The light source 12 is positioned to produce a light beam 24 that is aimed at the beam splitter 14. The beam splitter 14 splits the light beam 24 into two light beams 26, 28 and directs one of the light beams 26 toward the reflector 16 and the other light beam 28 toward the slide 22. The reflector 16 redirects light beam 26 toward the slide 22. The light beams 26, 28 are focused near the particles and aimed to interfere with each other to create a light intensity pattern near the particles.

The motor 18 can be used to move or rotate the reflector 16, which causes the light intensity pattern to move in space. A control system 19 is connected to the motor 18 to control operation of the motor 18. By moving the light intensity pattern in space and keeping the slide 22 fixed, forces created on the particles by the light intensity pattern cause the particles to move at velocities related to each particle's physical properties as described herein. The particles can also be caused to move by fixing the light intensity pattern in space and mechanically moving the slide 22 carrying the particles. This causes the light intensity pattern to move in space relative to the particles.

Alternatively, motor 18 can be connected to the light source 12 and beam splitter 14. In this embodiment the light source 12 and beam slitter 14 can be moved or rotated by the motor 18. This causes light beam 28 to move relative to light beam 26, which, in turn, causes the light intensity pattern to move.

Figure 1B:
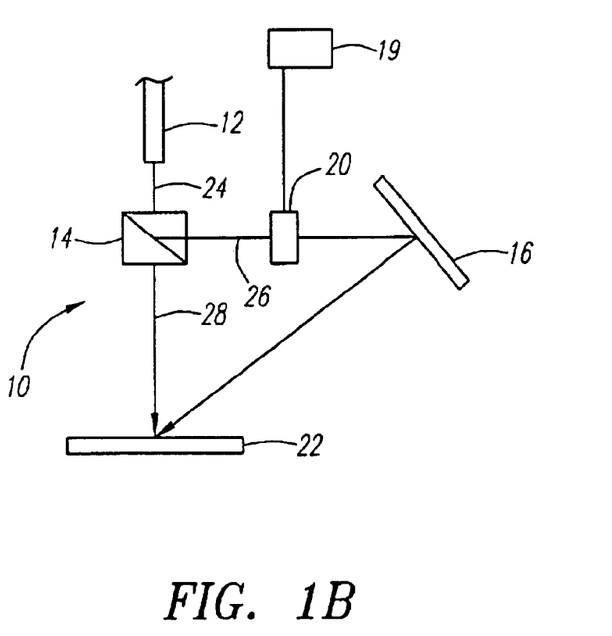

In another embodiment, shown in FIG. 1B, the light intensity pattern is moved by modulating the relative phase of the light beams 26, 28. In this embodiment, a phase modulator 20 is positioned in the path of light beam 26. The phase modulator 20 is configured to modulate the phase of light beam 26 relative to the phase of light beam 28. A control system 19 is connected to the phase modulator 20 for controlling operation of the phase modulator 20. Alternatively, the phase modulator 20 can be positioned in the path of light beam 28 for modulating the phase of light beam 28 relative to the phase of light beam 26.

Modulating the phases of light beams 26 and 28 relative to each other causes the light intensity pattern created by the interference of light beams 26 and 28 to move. Moving the light intensity pattern relative to the particles creates forces on the particles related to the physical properties of each particle. As described above, these forces will cause particles with different physical properties to move at different relative velocities.

Alternatively, an amplitude modulator can be used instead of the phase modulator 20. The amplitude modulator can be used for modulating the amplitude of the light beams 24, 26, 28 thus creating a moving light intensity pattern.

Preferably, the light source 12 comprises a laser for producing a light beams 26 and 28 coherent with respect to each other. Alternatively, two light sources could be used to product light beams 26 and 28.

In applications where the particles are biological material or living cells, it is preferable that the laser produce light beams 26, 28 having a wavelength of between 0.3 µm and 1.8 µm so as not to generate excessive heat that could damage the particles. More preferably, the laser would produce light beams 26, 28 having a wavelength of greater than 0.8 µm. Very good lasers are commercially available which produce light beams 26, 28 having a wavelength of 1.55 µm and would be appropriate for use in a system 10 according to the present invention. Alternatively, the light source 12 can produce incoherent light beams 26, 28.

Figure 2A:
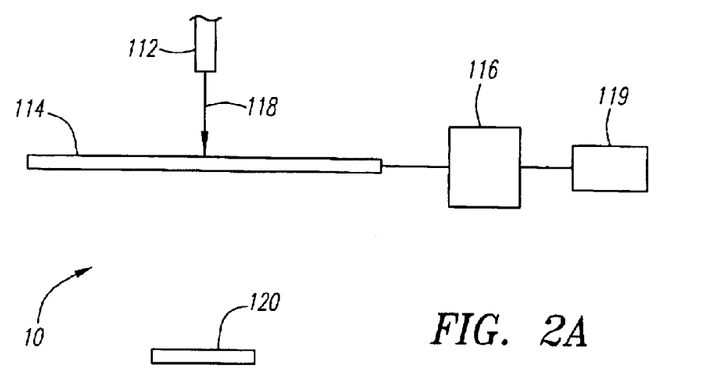

In another embodiment of the invention, shown in FIG. 2A, the system 110 comprises a light source 112 and an optical mask 114. A motor 116 can be connected to the light source 112 and optical mask 114 for moving or rotating the light source 112 and optical mask 114. A control system 119 is connected to the motor 116 for controlling operation of the motor 116 and thus movement of the light source 112 and optical mask 114. In this embodiment, the light source 112 produces a light beam 118 that is aimed through the optical mask 114 toward a slide 120 holding the particles to be separated.

The optical mask 114 is configured to create a light intensity pattern near the particles. The motor 116 can be used to move or rotate the light source 112 and optical mask 114 thus causing the light intensity pattern to move. Alternatively, the light intensity pattern can be fixed in space and the slide 120 can be moved producing relative motion between the light intensity pattern and the particles.

The optical mask 114 can comprise an optical phase mask, an optical amplitude mask, a holographic mask or any similar mask or device for creating a light intensity pattern. In another alternative embodiment, the optical mask 114 can be specially configured to produce a moving light intensity pattern. This type of optical mask 114 can be produced by writing on the mask with at least two light beams. In essence, one light beam writes on the mask to create the light intensity pattern and the other mask erases the mask. In this embodiment, a new light intensity pattern is created each time the mask is written upon.

Figure 2B:
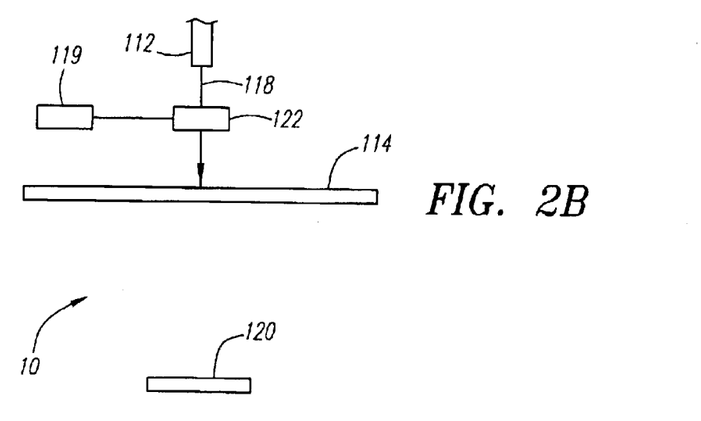

In the embodiment shown in FIG. 2B, a phase modulator 122 is used to create the moving light intensity pattern. The phase modulator 122 is positioned between the light source 112 and the optical mask 114 such that light beam 118 is directed through the phase modulator 112. A control system 119 is connected to the phase modulator 122 for controlling operation of the phase modulator 112.

Figure 3:
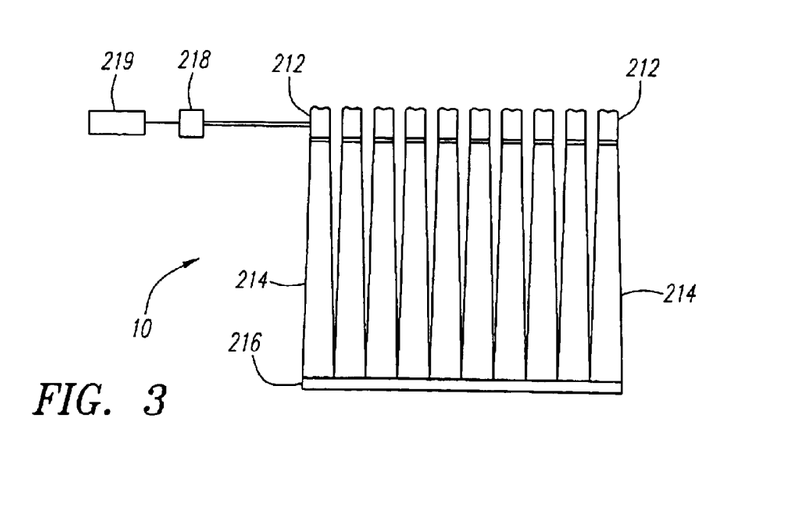

In yet another embodiment, shown in FIG. 3, the system 10 comprises a plurality of light sources 212 positioned adjacent to each other such that they produce light beams 214 directed toward a slide 216 holding the particles to be separated. In one embodiment, the light sources 212 are aimed to create light beams 214 that overlap each other to produce a light intensity pattern.

An actuator 218 can be attached to the light sources 212 for moving or rotating the light sources 212 to move the light intensity pattern with respect to the slide 216. A control system 219 is connected to the actuator 218 for controlling operation of the actuator 218. For example, motors (not shown) can be attached to each of the light sources 212. The light intensity pattern can also be moved relative to the slide 216 by modulating phase, moving the slide 216 relative to the light sources 212 or in any other described herein.

Alternatively, the light sources 212 can be aimed such that the light beams 214 slightly overlap each other near the slide 216. A light intensity pattern can be created by switching the light sources to be dimmed and brightened in certain patterns to give the appearance of a moving light intensity pattern. For example, in one embodiment the light sources 212 are dimmed and brightened such that at any given moment in time, whenever one light source is bright, all adjacent light sources are dim and when the first light source is dim the adjacent light sources are bright.

In operation, focusing a light beam in the vicinity of a particle causes the light beam to interact with optical dipoles inside the particle. Maximum intensity of a light beam is achieved at the focal point of the beam. The particle tends to move toward the point of maximum intensity of the light beam because the minimum energy for the overall system is achieved when the dipoles of the particle reside where the maximum intensity of the light beam occurs.

Figure 4A:
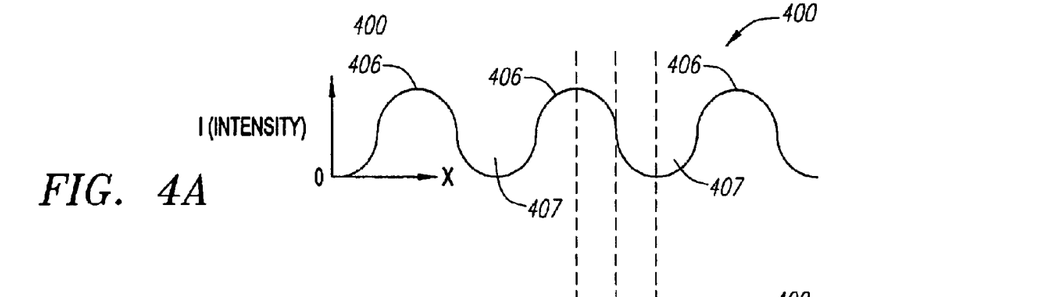
FIG. 4A is a graphical depiction of an optical grating produced light intensity pattern generated by a system according to the present invention.
Figure 4B:
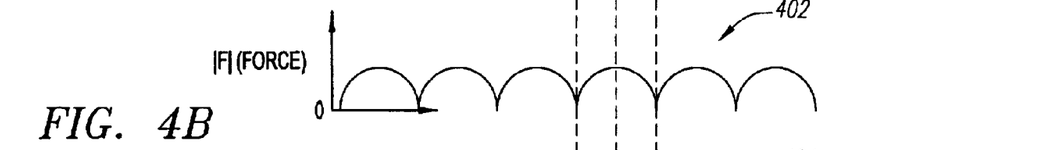
FIG. 4B is a graphical depiction of a energy pattern corresponding to the light intensity pattern of FIG. 4A.
Figure 4C:
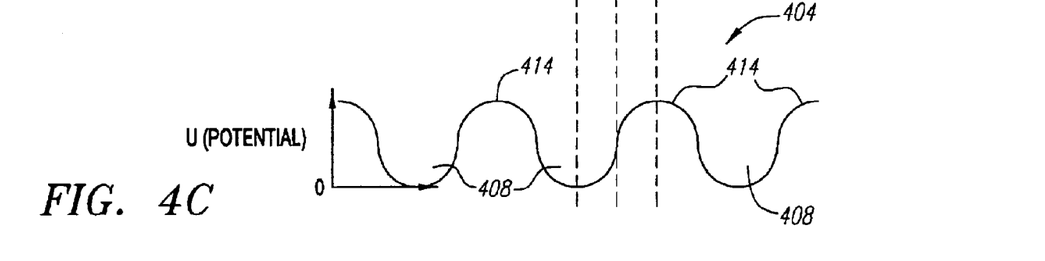
FIG. 4C is a graphical depiction of a potential energy pattern corresponding to the light intensity pattern of FIG. 4A.

A system according to the present invention, such as those described infra, are configured to create a variable light intensity pattern. FIGS. 4A, 4B, and 4C show a periodic light intensity pattern 400, the force 402 exerted on a particle by the light intensity pattern 400, and the potential 404 exerted on a particle by the light intensity pattern 400, respectively. The light intensity pattern 400 shown in FIG. 4A is sometimes referred to as an optical grating.

Particles subjected to the light intensity pattern 400 of FIG. 4A tend to move toward the peak intensity points 406. The wells 408 of the potential pattern 404 shown in FIG. 4C represent points where the overall system energy is at a minimum. Thus, a particle will tend to move toward the wells 408 of the potential pattern 404.

Light intensity patterns 400 created according to the present invention can comprise at least two peaks 406 and at least two valleys 407. Suitable light intensity patterns 400 can be periodic, sinusoidal, nonsinusoidal, constant in time or varying in time. If the light intensity pattern 400 is periodic, the period can be optimized to create separation between particles exposed to the light intensity pattern 400. For example, for large particles the period length can be increased to increase the size of wells 408 in the corresponding potential pattern 404 to accommodate the large particles.

Figure 5A:
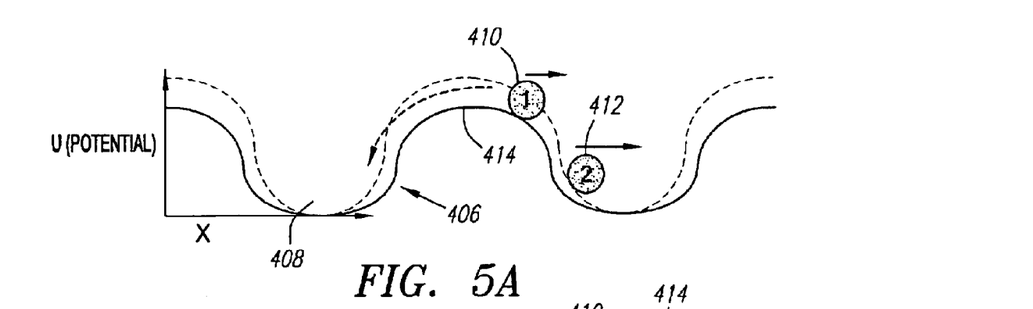
FIGS. 5A, 5B and 5C are a graphical depiction of a moving potential energy pattern generated by a system and method according to the present invention.
Figure 5B:
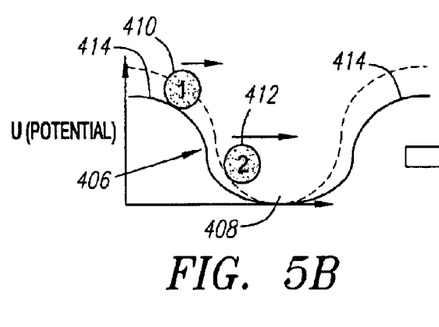
Figure 5C:
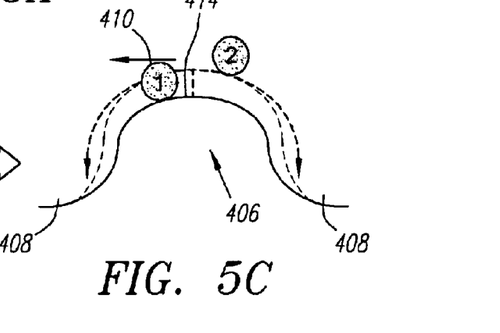

FIGS. 5A, 5B and 5C show two particles 410, 412 exposed to a potential pattern 406. In this figure, particles 410 and 412 are of similar size and shape but have different dielectric constants.

As described infra, moving the light intensity pattern 400 and consequently the potential 406 created by the light intensity pattern 400, relative to particles 410, 412 exposed to the light intensity pattern 400 causes the particles 410, 412 to move at velocities related to the physical properties of the particles 410, 412. For example, the force acting on a particle is proportional to the dielectric constant of the particle. More specifically, the force is proportional to $(E_p - E_m)/(E_p + 2 E_m)$. Thus, two particles 410, 412 of similar size and shape having different dielectric properties will travel at different velocities when exposed to a moving light intensity pattern 400.

The potential 406 created by the light intensity pattern 400 causes the particles 410, 412 to move toward wells 408 in the potential pattern 406. Because the light intensity pattern 400, and consequently the potential pattern 406, are moving, the particles 410, 412 "surf" on waves created in the potential pattern 406. The waves include peaks 414 of high potential and wells 408 of low potential.

The particles 410, 412 move with the potential pattern 406 at velocities related to the particles 410, 412 physical properties. One such physical property is the dielectric constant of the particles 410, 412. Because the dielectric constants of particles 410 and 412 are different, they will move at different velocities when exposed to the potential pattern 406 created by the light intensity pattern 400.

In one embodiment, the light intensity pattern 400, and consequently the potential pattern 406, is moved at a constant velocity. The velocity can be optimized to cause separation of the particles 410, 412 based on the particles' 410, 412 physical properties. For example, a maximum velocity exists for each particle 410, 412 such that if the maximum velocity is exceeded, the peak 414 on which the particle 410 or 412 is "surfing" will pass the particle 410 or 412 causing the particle 410 or 412 to fall into the preceding well 408.

In this embodiment, a velocity is chosen between the maximum velocities of particles 410 and 412. Assuming the maximum velocity of particle 412 is higher than the maximum velocity of particle 410, when exposed to the potential pattern 406 shown in FIG. 5A, particle 412 will "surf" on peak 414 and particle 410 will fall behind into well 408 thus separating particles 410 and 412 based on their physical properties.

In another embodiment is shown in FIGS. 5B and 5C. In this embodiment, particles 410 and 412 are exposed to potential pattern 406 for a predetermined amount of time to allow the particles 410, 412 to separate slighted as shown in FIG. 5B. Once the particles 410, 412 have separated slightly, the potential pattern 406 is "jerked" forward a predetermined difference such that the particles 410, 412 are positioned on opposites sides of peak 414. Once the particles are positioned on opposite sides of peak 414, the forces exerted on the particles 410, 412 cause them to fall into wells 408 on opposite sides of peak 414 thus separating the particles 410 and 412 based on their physical properties.

Figure 6:
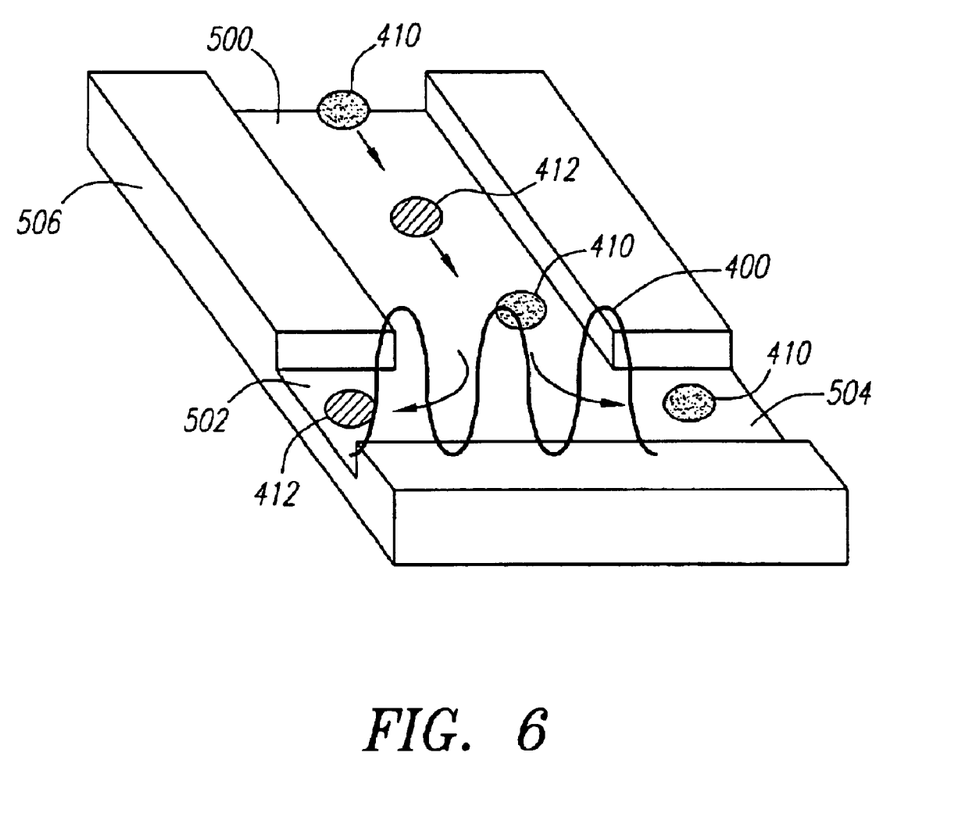
FIG. 6 is an enlarged sectional view of a fluidic microchannel with a graphical depiction of the moving light intensity pattern of FIG. 4A superimposed in the fluidic micro-channel.

In one application of the invention, shown in FIG. 6, a moving light intensity pattern 400 can be superimposed onto a fluidic channel guided medium 506 having fluidic channels 500, 502 and 504. The channels 500, 502 and 504 are arranged in a T-shape with the light intensity pattern 400 being superimposed on the branch of the "T" (i.e. the junction between channels 500, 502, and 504).

The particles 410, 412 travel from channel 500 into the light intensity pattern 400. The light intensity pattern 400 is configured to move particles 410 and 412 in different directions, as described infra, based on the particles' 410, 412 physical properties. In this case, the light intensity pattern 400 is configured to move particle 412 into channel 502 and particle 410 into channel 504. In this manner, the particles 410, 412 can be separated and collected from their corresponding channels 504, 502, respectively.

Using an application such as this, the light intensity pattern can be configured to move particles 410 having a physical property below a certain threshold into one channel 504 and particles 412 having a physical property above the threshold into the other channel 502. Thus, various particles can be run through channel 500 and separated based on a certain threshold physical property. Multiple fluidic channel guided mediums 500 can be connected to channels 502 and/or 504 to further sort the separated particles 410, 412 based on other threshold physical properties.

Additional optimization can be done to facilitate particle sorting. For example, each particle 410, 412 has a specific resonant frequency. Tuning the wavelength of the light intensity pattern 400 to the resonant frequency of one of the particles 410 or 412 increases the force exerted on that particle 410 or 412. If, for example, the frequency of the light intensity pattern is tuned to the resonant frequency of particle 412, the velocity at which particle 412 travels is increases, thus increasing the separation between particles 410 and 412.

Other forces can also be superimposed onto the particles 410, 412 to take advantage of additional differences in the physical properties of the particles 410, 412. For example, a gradient, such as temperature, pH, viscosity, etc., can be superimposed onto the particles 410, 412 in either a linear or non-linear fashion. External forces, such as magnetism, electrical forces, gravitational forces, fluidic forces, frictional forces, electromagnetic forces, etc., can also be superimposed onto the particles 410, 412 in either a linear or non-linear fashion.

The light intensity pattern 400 and/or additional forces can be applied in multiple dimensions (2D, 3D, etc.) to further separate particles 410, 412. The period of the light intensity pattern 400 can be varied in any or all dimensions and the additional forces can be applied linearly or non-linearly in different dimensions.

A monitoring system, not shown, can also be included for tracking the separation of the particles 410, 412. The monitoring system can provide feedback to the system and the feedback can be used to optimize separation or for manipulation of the particles 410, 412.

It will be apparent to those skilled in the art that modifications may be made without departing from the spirit and scope of the invention. Accordingly, it is not intended that the invention be limited except as may be necessary in view of the appended claims.

What is claimed is:

1. A method for separating at least two particles, the particles having different dielectric constants, the method comprising the steps of:

applying a light source to create a light intensity pattern;

exposing the at least two particles to the light intensity pattern producing force on each particle;

moving the light intensity pattern with respect to the at least two particles causing the at least two particles to move with the light intensity pattern at velocities related to their respective dielectric constants, wherein each of the at least two particles moves at a different velocity causing the at least two particles to separate.

2. The method according to claim 1, wherein the step of applying a light source further comprises interfering at least two optical light beams.

3. The method according to claim 2 wherein the at least two optical light beams are coherent light beams.

4. The method according to claim 2 wherein the at least two optical light beams are incoherent light beams.

5. The method according to claim 2 further comprising splitting one optical light beam to create the at least two optical light beams.

6. The method according to claim 1 wherein the step of applying a light source further comprises using an optical mask to create the light intensity pattern.

7. The method according to claim 6 wherein the optical mask comprises an amplitude mask.

8. The method according to claim 6 wherein the optical mask comprises a phase mask.

9. The method according to claim 6 wherein the optical mask comprises a holographic mask.

10. The method according to claim 1 wherein the step of applying a light source further comprises periodically dimming and brightening a plurality of light sources to create the light intensity pattern.

11. The method according to claim 1 wherein the light intensity pattern comprises at least two peaks.

12. The method according to claim 1 wherein the light intensity pattern comprises at least two valleys.

13. The method according to claim 1 wherein the light intensity pattern is sinusoidal.

14. The method according to claim 1 wherein the light intensity pattern is periodic but not sinusoidal.

15. The method according to claim 1 wherein the light intensity pattern is constant in time.

16. The method according to claim 1 wherein the light intensity pattern varies in time.

17. The method according to claim 1 wherein the light intensity pattern is periodic and the period is optimized to create separation between the at least two particles.

18. The method according to claim 1 wherein the light intensity pattern is generated with coherent optical beams and the step of moving the light intensity pattern further comprises modulating the phase of the light beam(s).

19. The method according to claim 1 wherein the light intensity pattern is moved at a constant velocity.

20. The method according to claim 1 further comprising optimizing velocity of the light intensity pattern to cause separation based on the dielectric constants of the at least two particles.

21. The method according to claim 1 further comprises after allowing the at least two particles to separate, altering velocity of the light intensity pattern with respect to the at least two particles causing further separation of the at least two particles.

22. The method according to claim 1 wherein the light source has a wavelength of between 0.3 $\mu$m and 1.8 $\mu$m.

23. The method according to claim 22 wherein the wavelength is between 0.8 $\mu$m and 1.8 $\mu$m.

24. The method according to claim 23 wherein the wavelength is exactly or approximately 1.55 $\mu$m.

25. The method according to claim 1 wherein at least one of the at least two particles have a resonant frequency and the light intensity pattern has a wavelength tuned to the resonate frequency of one of the at least two particles.

26. The method according to claim 1 wherein the light intensity pattern is two-dimensional.

27. The method according to claim 26 wherein the light intensity pattern has a period in each of the two dimensions and the period is different in each dimension.

28. The method according to claim 1 wherein the light intensity pattern is three-dimensional.

29. The method according to claim 28 wherein the light intensity pattern has a period in each of the three dimensions and the period is different in at least two of the dimensions.

30. The method according to claim 1 wherein the at least two particles are carried in a medium.

31. The method according to claim 30 wherein the medium is a fluidic medium.

32. The method according to claim 31 wherein the medium is non-guided.

33. The method according to claim 31 wherein the medium is guided.

34. The method according to claim 33 wherein the guided medium includes fluidic channels.

35. The method according to claim 1 further comprising the step of superimposing a gradient onto the light intensity pattern.

36. The method according to claim 35 wherein the gradient is spatially constant.

37. The method according to claim 35 wherein the gradient is spatially varying.

38. The method according to claim 35 wherein the gradient is temperature.

39. The method according to claim 35 wherein the gradient is pH.

40. The method according to claim 35 wherein the gradient is viscosity.

41. The method according to claim 1 further comprising the step of superimposing an external force onto the light intensity pattern.

42. The method according to claim 41 wherein the force is constant.

43. The method according to claim 41 wherein the force is varying spatially and/or temporally.

44. The method according to claim 41 wherein the force is magnetic.

45. The method according to claim 41 wherein the force is electrical.

46. The method according to claim 41 wherein the force is gravitational.

47. The method according to claim 41 wherein the force is fluidic.

48. The method according to claim 41 wherein the force is frictional.

49. The method according to claim 44 wherein the force is electromagnetic.

50. The method according to claim 1 further comprising the step of monitoring separation of the at least two particles.

51. The method according to claim 50 further comprising providing feedback regarding particle separation.

52. The method according to claim 1 wherein the particles are cells.

53. The method of sorting particles in a branched microfluidic device comprising the steps of:
providing a device having a main channel, a first branch channel, and a second branch channel;
flowing a plurality of particles down the main channel;
superimposing a moving light intensity pattern on the device at a junction between the main channel, the first branch channel, and the second branch channel causing at least some of the plurality of particles to be directed into the first branch channel and at least some of the plurality of particles to be directed into the second branch channel, wherein the sorting of the particles into the first branch channel and the second branch channel is based at least in part on the dielectric constants of the particles.

54. The method of claim 53 wherein the particles are cells.

55. The method of claim 53 wherein the main channel; the first branch channel, and the second branch channel intersect to form a T.

56. The method of claim of claim 53 wherein particles having a dielectric constant below a threshold level are directed into the first branch channel and particles having a dielectric constant above a threshold level are directed to a second branch channel.

57. The method of claim 53 comprising the additional step of further sorting the particles in one or both of the first branch channel and the second branch channel.

58. The method of claim 53 further comprising the step of monitoring the separation of the particles into the first branch channel and the second branch channel.

* * * * *